United States Patent
Huang et al.

(10) Patent No.: US 6,739,180 B2
(45) Date of Patent: May 25, 2004

(54) INTELLIGENT GAS IDENTIFICATION SYSTEM AND METHOD THEREOF

(75) Inventors: Yi-Shiao Huang, Hsinchu (TW); I-Cherng Chen, Hsinchu (TW); Chien-Hsiung Tai, Taipei (TW); Wen-Yuan Tsai, Taichung (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 10/383,563

(22) Filed: Mar. 10, 2003

(65) Prior Publication Data

US 2004/0040371 A1 Mar. 4, 2004

Related U.S. Application Data

(63) Continuation-in-part of application No. 10/283,260, filed on Oct. 30, 2002.

(30) Foreign Application Priority Data

Aug. 30, 2002 (TW) ........................................ 91119779 A

(51) Int. Cl.$^7$ ............................................. G01N 27/00
(52) U.S. Cl. ........................................ 73/31.06; 73/23.2
(58) Field of Search ............................... 73/23.2, 25.01, 73/25.05, 31.06; 422/98; 702/24

(56) References Cited

U.S. PATENT DOCUMENTS

| 5,987,963 A | * 11/1999 | Stormbom | 73/25.01 |
| 6,029,090 A | * 2/2000 | Herbst | 607/66 |
| 2001/0032054 A1 | * 10/2001 | Kimoto et al. | 702/24 |

FOREIGN PATENT DOCUMENTS

| GB | 2369730 | * 6/2002 | H05B/33/08 |
| JP | 406082407 | * 3/1994 | 422/98 |
| JP | 406130017 | * 5/1994 | 422/98 |

* cited by examiner

Primary Examiner—Daniel S. Larkin
(74) Attorney, Agent, or Firm—Birch, Stewart, Kolasch & Birch, LLP

(57) ABSTRACT

An intelligent gas identification system and method of gas identification in a specific environment. The intelligent gas identification system has a sensor, a pulse power supply module, and a processing device in which a plurality of chemical matter characteristics signals is stored. When the sensor is disposed in the specific environment, the pulse power supply module sends a variable pulse-amplitude-modulated voltage to the sensor, so that the sensor outputs a signal to the processing device. The processing device compares the outgoing signal to the chemical matter characteristics signals to determine an identification result for the gas.

13 Claims, 6 Drawing Sheets

INTELLIGENT GAS IDENTIFICATION SYSTEM AND METHOD THEREOF

CROSS REFERENCE TO RELATED APPLICATION

This application is a continuation-in-part of copending application Ser. No. 10/283,260 filed on Oct. 30, 2002, the entire contents of which are hereby incorporated by reference and for which priority is claimed under 35 U.S.C. §120.

BACKGROUND OF THE INVENTION

1. Field of the Invention

The present invention relates to an intelligent gas identification system and a method of gas identification for gas or volatile chemical matters in a specific environment.

2. Description of the Related Art

Conventionally, a gas concentration sensor is used for obtaining concentration for a specific gas. An example of a conventional gas concentration sensor 500 is described in detail with reference to FIG. 1a and FIG. 1b.

The conventional gas concentration sensor 500, as shown in FIG. 1a, has a body 510, voltage input elements 520, and output elements 530. The body 510, as shown in FIG. 1b, has a substrate 512, electrodes 514, a sensing element 516, and a heater 518. Generally, the sensing element 516 is a membrane of metallic oxide, such as a membrane of tin dioxide ($SnO_2$), which reacts to a specific gas in the vicinity of the gas concentration sensor 500. When the conventional gas concentration sensor 500 is applied in a specific environment to perform gas concentration measurement, a fixed voltage is input to the sensor 500 through the voltage input element 520 to activate the heater 518, so that the membrane of the sensing element 516 is heated to a predetermined temperature, such as 400° C. Thus, the membrane of the sensing element 516 reacts to the specific gas to be measured in the specific environment, and the resistance of the sensing element 516 is changed due to the reaction. Then, an outgoing voltage, determined by the resistance of the sensing element 516, is obtained through the output element 530 as an outgoing signal.

It is obvious that the concentration of the specific gas in the specific environment affects the reaction, and the relation between the concentration of the specific gas and the resistance of the sensing element 516 can be established by experiment as a reference of the gas concentration sensor 500.

FIG. 2 is a chart showing an example of the gas concentration measurement with the conventional gas concentration sensor 500, in which the curves L1 and L2 respectively refer to different concentrations of the specific gas. When the voltage is input to the sensor 500 through the voltage input element 520 to activate the heater 518, the membrane of the sensing element 516 is heated to a predetermined temperature, such as 400° C. In both cases, the resistance of the sensing element 516 is changed due to the reaction, which induced to the outgoing voltages shown as point A to concentration L1 and point B to concentration L2. It should be noted that the predetermined temperature of the conventional gas concentration sensor 500 is generally set to a preferred temperature, in which the outgoing voltage is significant, so that responses of the gas concentration sensor 500 are obvious. Fox example, the preferred temperature shown in FIG. 2 is approximately 400° C.

The conventional gas concentration sensor 500 has a membrane-type structure, which has a relatively low cost. Further, the conventional gas concentration sensor 500 reacts to the gas to be measured in a short time and can be used effectively for a long period of time. As a result, the gas concentration sensor is widely used in various situations. For example, U.S. Pat. No. 6,336,354 discloses a gas concentration measuring apparatus, in which a gas concentration sensor is applied, that uses a heat control circuit to supply power to the heater of the sensor cyclically using a pulse-amplitude-modulated (PAM) signal. In this case, the apparatus corrects errors contained in the gas concentration signal, so that the signal is regulated, and the outgoing signal of the gas concentration sensor is significant.

However, the conventional gas concentration sensor 500 is used mainly to measure the concentration of a specific gas. It is obvious that the conventional gas concentration sensor 500 can be used in a specific environment when the specific gas exists in the specific environment. However, the membrane of gas concentration sensor 500 may react to a plurality of gases. Thus, when more than one of the gases exists in the specific environment, the conventional gas concentration sensor 500 does not distinguish between each gas, so that the outgoing signal of the gas concentration sensor 500 does not correspond exactly to a specific gas among the multiple gases, and concentrations are not obtained accurately. Additionally, when the composition of the gas in the specific environment is completely unidentified, the conventional gas concentration sensor 500 does not distinguish the composition of the gas.

SUMMARY OF THE INVENTION

In view of this, the present invention relates to an intelligent gas identification system and method thereof, in which a pulse-amplitude-modulated (PAM) signal is used as the input voltage to the conventional gas concentration sensor so that the outgoing signals corresponding to various gases differ. Thus, a chemical matter characteristics database can be established by experiment, and the chemical matter characteristics can be used as a reference fingerprint of composition and/or concentration of the gases.

The present invention discloses an intelligent gas identification system. The intelligent gas identification system has a sensor, a pulse power supply module, and a processing device. The sensor has a voltage input element, an output element and a sensing element and is disposed in a specific environment to perform gas identification. The pulse power supply module is connected to the voltage input element to send a variable pulse-amplitude-modulated voltage to the sensor through the voltage input element, so that the sensor outputs an outgoing signal through the output element. The processing device stores a plurality of chemical matter characteristics signals and receives the outgoing signal from the output element of the sensor, then compares the outgoing signal with the chemical matter characteristics signals to determine an identification result for the gas.

Further, the present invention discloses a method of gas identification. First, a sensor is provided in a specific environment. The sensor is provided with a variable pulse-amplitude-modulated voltage, so that the sensor outputs an outgoing signal corresponding to gas in the specific environment. Then, the outgoing signal is compared with a plurality of chemical matter characteristics signals to determine an identification result for the gas in the specific environment.

In the method of gas identification, the chemical matter characteristics signals can be obtained by exsposing the sensor to a plurality of predetermined chemical matters and sending a variable pulse-amplitude-modulated voltage to the sensor respectively, so that the sensor outputs each of the chemical matter characteristics signals corresponding to each of the predetermined chemical matters. Then, the chemical matter characteristics signals can be stored in a database.

In the system and method of the present invention, the outgoing signal can be a pulse amplitude voltage signal. Further, the sensing element can be a membrane of a metallic oxide, such as tin dioxide ($SnO_2$). Further, the identification result for the gas can be composition and/or concentration of the respective constituents of the gas.

BRIEF DESCRIPTION OF THE DRAWINGS

The present invention can be more fully understood by reading the subsequent detailed description in conjunction with the examples and references made to the accompanying drawings, wherein.

DETAILED DESCRIPTION OF THE INVENTION

In gas concentration measurement, a fixed voltage is input to a sensor to activate a heater, so that the membrane of the sensing element is heated to perform reaction to the specific gas to be measured in the specific environment, and the resistance of the sensing element is changed due to the reaction. Thus, an outgoing signal is obtained. The fixed voltage is generally set to heat the membrane of the sensing element to a preferred temperature. However, if the voltage input to the sensor is changed, the outgoing signal is also changed.

Figure 3:
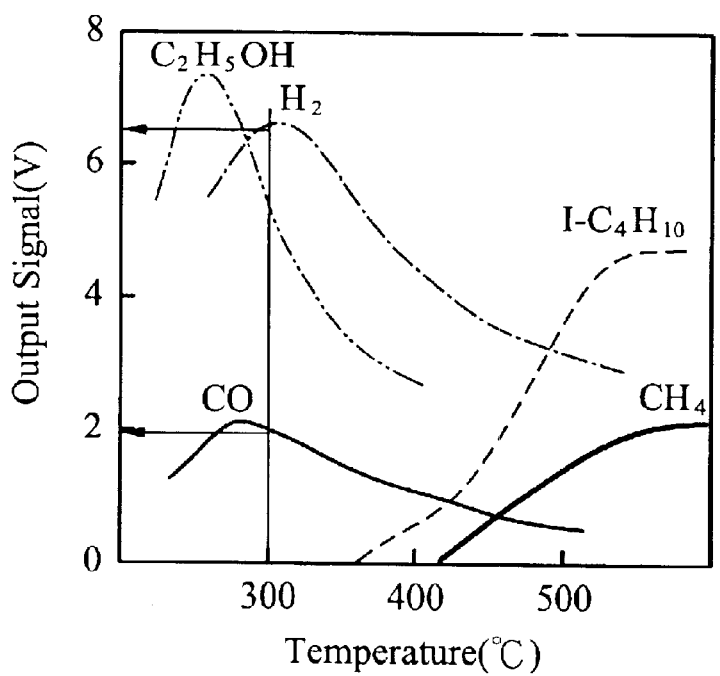
FIG. 3 is a chart showing the outgoing signals corresponding to various gases as output by the conventional gas concentration sensor.

FIG. 3 is a chart showing the outgoing signals corresponding to a plurality of gases measured by a sensor. The gases include hydrogen ($H_2$), carbon monoxide (CO), ethanol ($C_2H_5OH$), methane ($CH_4$) and butane ($C_4H_{10}$), and the concentration of each gas is kept at 0.1% to obtain the outgoing signals. The sensor applied is a widely-used conventional gas concentration sensor as described above. It should be noted that the curves of FIG. 3 show that the outgoing signals of the gases change corresponding to the membrane temperature (that is, the voltage input to the sensor), and each outgoing signal can be recognized as a distinctive pattern. Thus, the outgoing signal of the gas can be used as a chemical matter characteristics signal of the gas in gas identification. This is exactly the concept introduced in the present invention.

Figure 2:
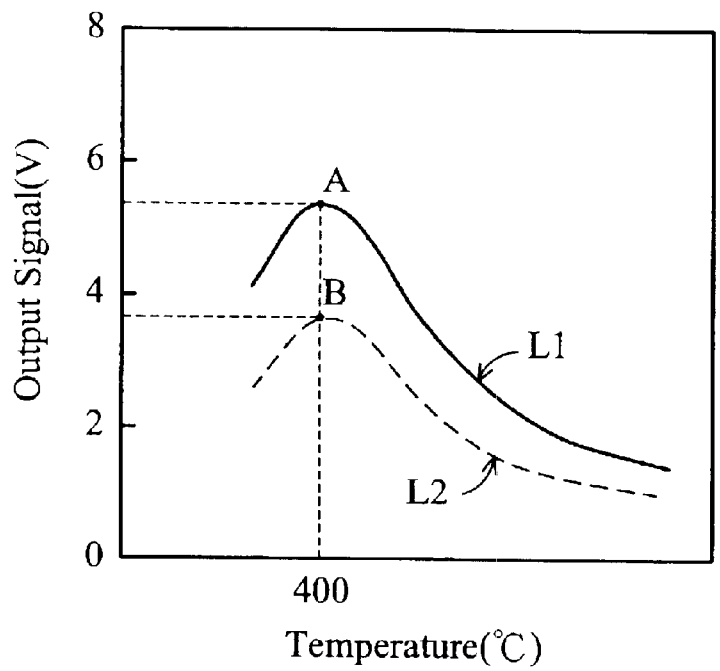
FIG. 2 is a chart showing the outgoing signals corresponding to a specific gas with various concentrations as output by the conventional gas concentration sensor.

The gas identification concept in FIG. 3 can be further described in comparison to the gas concentration measurement as shown in FIG. 2. In FIG. 2, the outgoing signal of the gas concentration sensor 500 is a point, related to a fixed membrane temperature (due to the fixed voltage input to the sensor 500), such as the preferred temperature. However, in FIG. 3, the outgoing signal of the sensor is a curve related to a specific range of membrane temperature, applied as the chemical matter characteristics signal of the gas and that can be used in gas identification.

Figure 4:
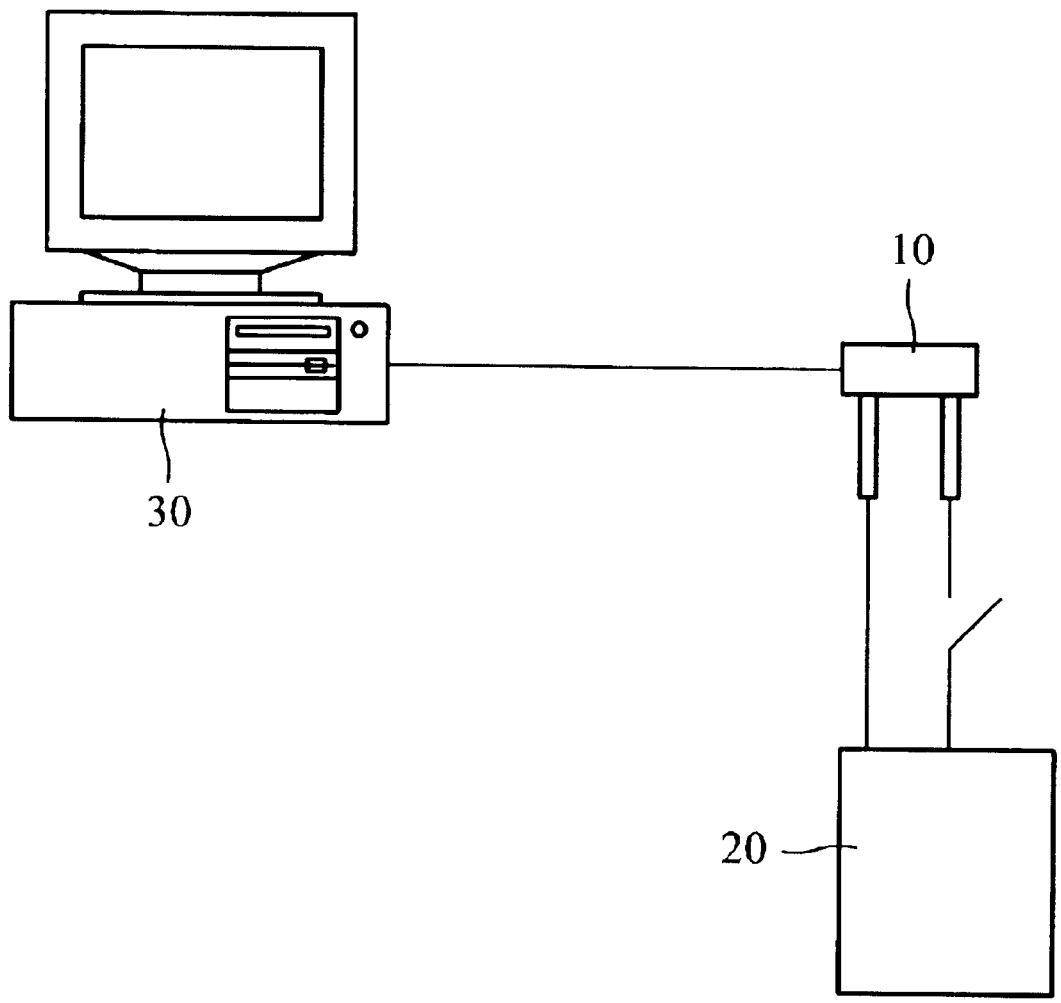
FIG. 4 is a schematic view showing an embodiment of the intelligent gas identification system of the present invention.

An embodiment of the intelligent gas identification system of the present invention is hereinafter described with reference to FIG. 4. The intelligent gas identification system of the present invention is applied to perform gas identification (or volatile chemical matter identification) in a specific environment. The intelligent gas identification system has a sensor 10, a pulse power supply module 20, and a processing device 30.

Figure 1A:
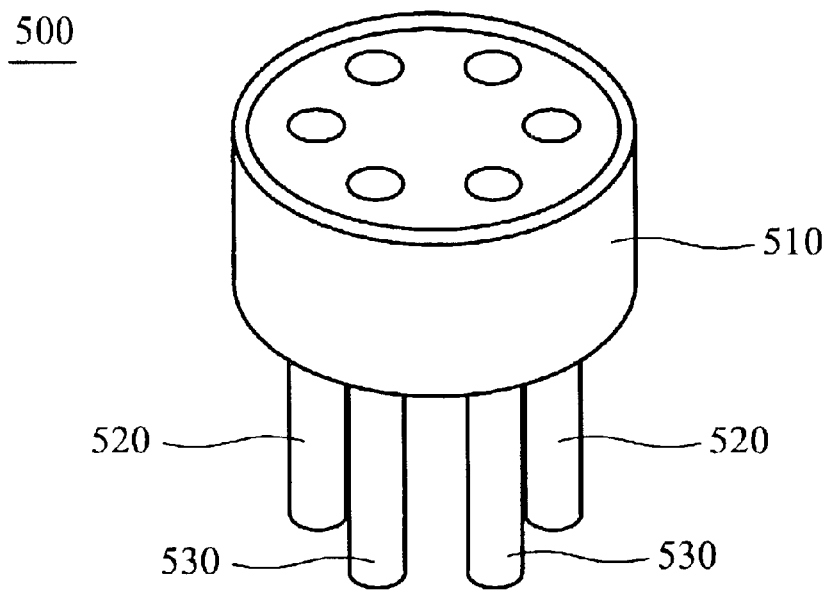
FIG. 1a is a schematic view of a conventional gas concentration sensor.
Figure 1B:
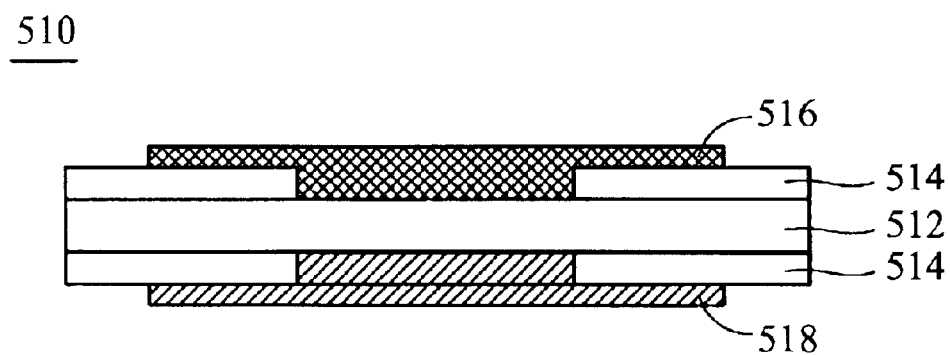
FIG. 1b is a schematic view of the body of the conventional gas concentration sensor.

The sensor 10, which can be a conventional gas concentration sensor 500 as shown in FIG. 1a, has at least a voltage input element, at least an output element, and a sensing element (that is, the body 510). The sensing element can be a membrane of metallic oxide, such as a membrane of tin dioxide ($SnO_2$), which reacts to the specific gas in the vicinity of the sensor 10.

The pulse power supply module 20 is connected to the voltage input element of the sensor 10 to send a variable pulse-amplitude-modulated voltage to the sensor 10, so that the sensor 10 sends out an outgoing signal through the output element.

The processing device 30 can be a computer with a pattern recognition module and a database for storing a plurality of chemical matter characteristics signals. The pattern recognition module, for example, can be graphic recognition software. Further, the processing device 30 receives an outgoing signal from the output element of the sensor 10.

When the intelligent gas identification system of the embodiment is used to perform gas identification, the sensor 10 is disposed in the specific environment. The pulse power supply module 20 sends a variable pulse-amplitude-modulated voltage to the sensor 10 through the voltage input element, so that the membrane of the sensing element is reiteratively heated, and in each heating process, the membrane temperature varies due to the variable pulse-amplitude-modulated voltage. Thus, the membrane reacts to the gas in the specific environment with different temperature, and the sensor 10 sends out an outgoing signal, such as a variable pulse-amplitude-modulated signal, to the processing device 30. Then, the processing device 30 compares the outgoing signal with the chemical matter characteristics signals to determine an identification result for the gas, such as composition of the gas, and/or concentration of the respective constituents of the gas.

Figure 5:
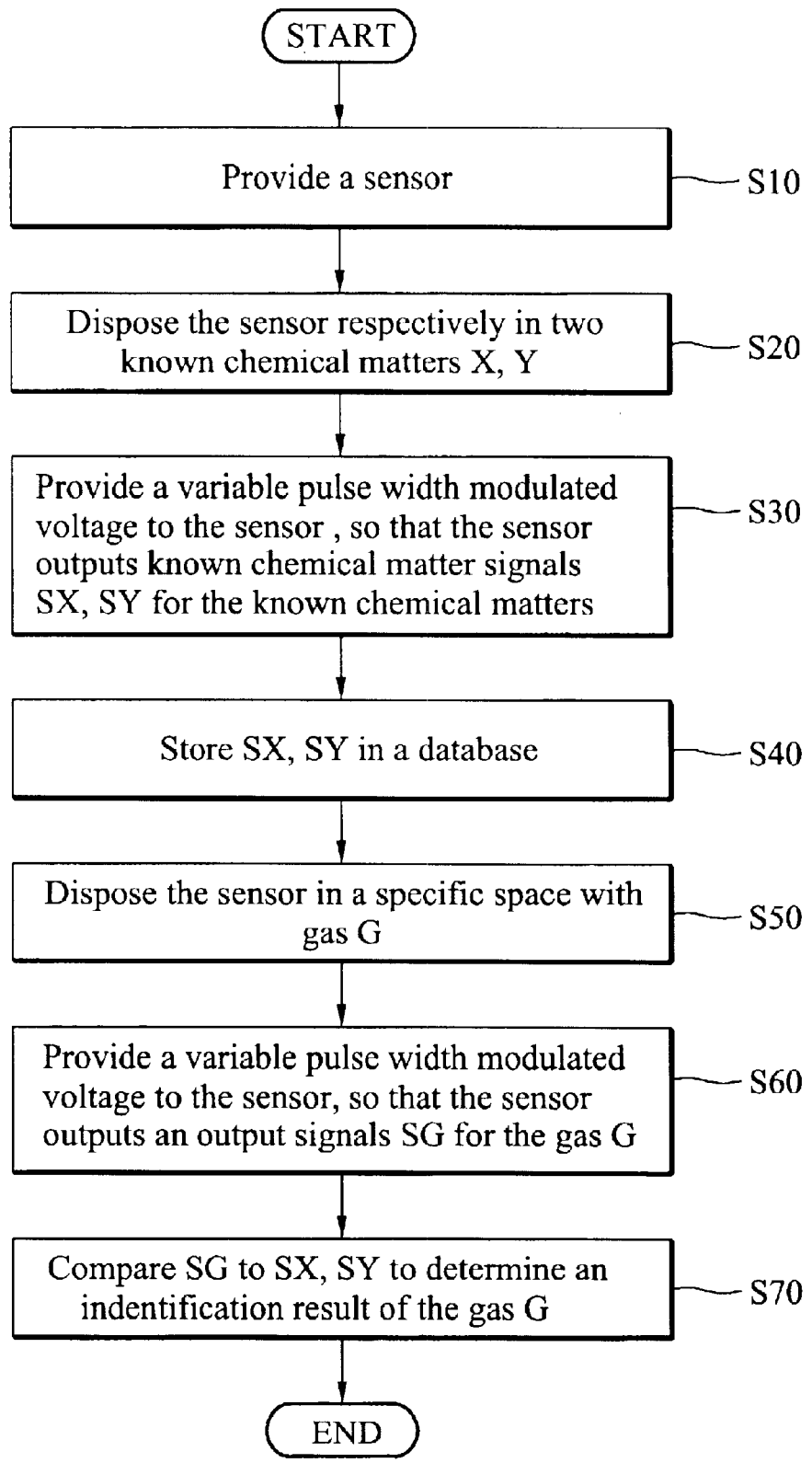
FIG. 5 is a flowchart showing the method of gas identification of the present invention.

A further embodiment of the method of gas identification of the present invention can be described with reference to the flowchart of FIG. 5. The embodiment assumes that a gas G exists in a specific environment to be identified, and two given chemical matters X and Y are applied for comparison to the gas G. That is, the gas identification is performed to determine if the gas G matches X or Y exactly.

When the gas identification is performed, a sensor 10 as mentioned is provided (step S10) and disposed in the given chemical matters X and Y (step S20). Then, a variable pulse-amplitude-modulated voltage is provided to the sensor 10 respectively, so that the sensor 10 outputs the chemical matter characteristics signals SX, SY for the given chemical matters X and Y (step S30). These chemical matter characteristics signals SX, SY can be stored in a database (step S40) for further gas identification of the gas G.

Then, the sensor is disposed in the specific environment with the gas G (step S50). The sensor is provided with a variable pulse-amplitude-modulated voltage, so that the sensor outputs an outgoing signal SG corresponding to the gas G in the specific environment (step S60). Thus, the processing device 30 receives the outgoing signal SG and compares the outgoing signal SG to the chemical matter characteristics signals SX and SY to determine an identification result for the gas G (step S70).

The identification result may be a value indicating that "the gas G matches X/Y exactly" or "the gas G matches neither of X and Y". It should be noted that, if the patterns (the chemical matter characteristics signals) of X and Y do not overlap, such as the distinct curves in FIG. 3, the gas identification can be performed to determine if the gas G is a mixed gas of X and Y, and the concentration of X and/or Y respectively.

Figure 6:
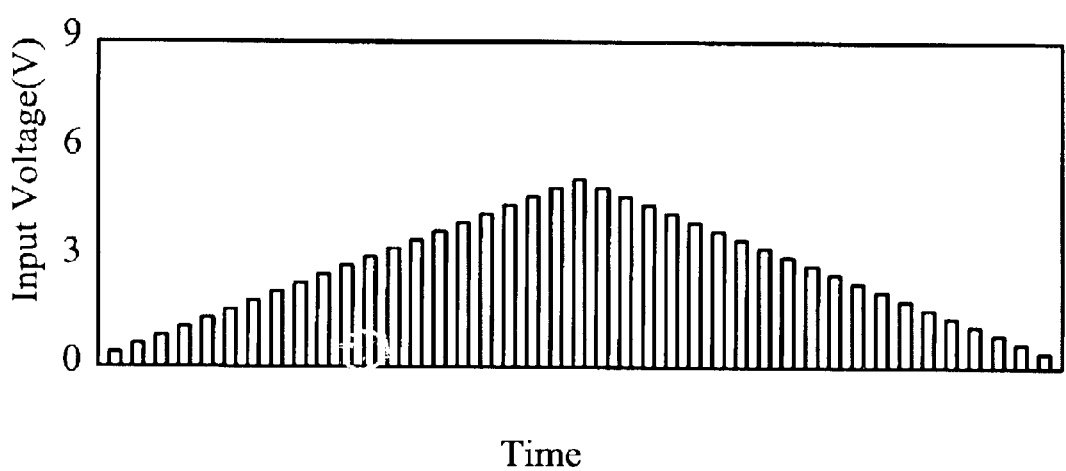
FIG. 6 is a schematic chart showing the variable pulse-amplitude-modulated voltage in the embodiment of the present invention.
Figure 7A:
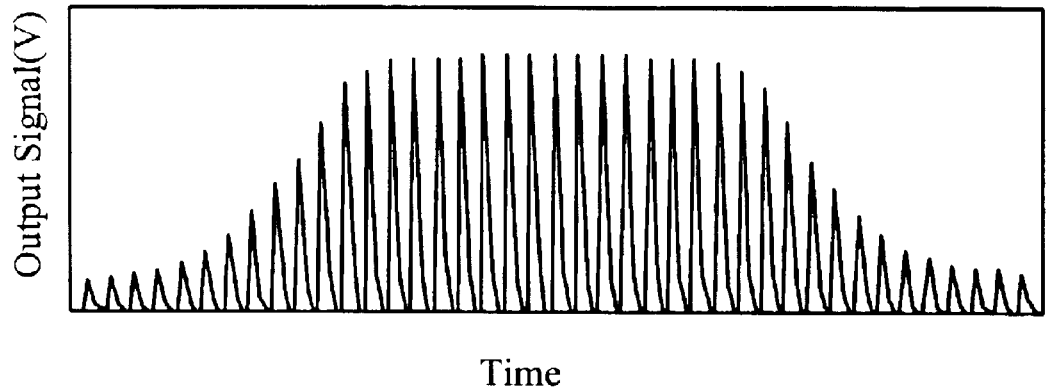
FIG. 7a is a chart showing a first embodiment of the outgoing signal obtained in the present invention.
Figure 7B:
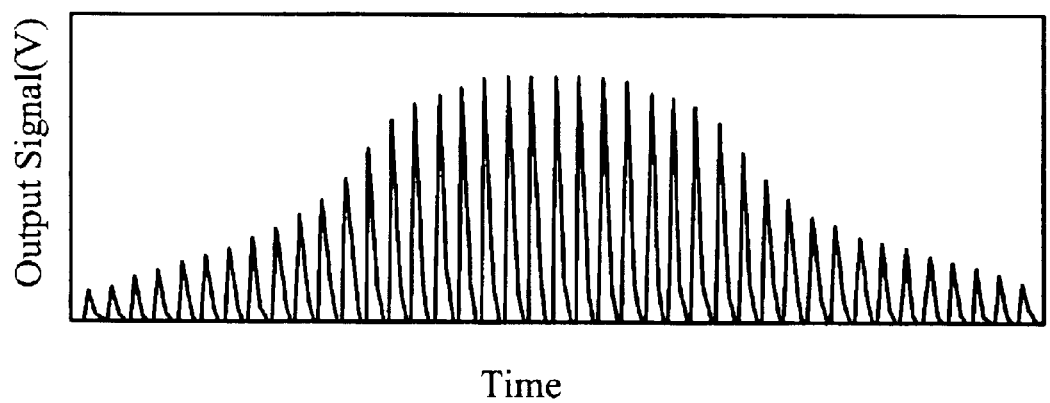
FIG. 7b is a chart showing a second embodiment of the outgoing signal obtained in the present invention.

An example of the variable pulse-amplitude-modulated voltage input to the sensor 10 of the intelligent gas identification system of the present invention is shown in FIG. 6. Further, two examples of the outgoing signals of the sensor 10 are shown in FIG. 7a and FIG. 7b.

It should also be noted that the chemical matter characteristics signals (the patterns) obtained in the present invention can be used as "fingerprints" of the predetermined gases. With graphic recognition techniques, the present invention can replicate the sense of smell in a more qualitative analytic way.

In the intelligent gas identification system of the present invention, the variable pulse-amplitude-modulated voltage is applied as the input voltage to the sensor 10, so that in each pulse of the PAM voltage, the input voltage returns to 0, and the membrane temperature returns to room temperature. Since the sensor reacts to the gas to be measured in a short time and can be used effectively over a long period of time, the present invention ensures that the outgoing signal corresponding to each pulse of the PAM voltage is an exact value, which enhances gas identification accuracy.

As well, it should be noted that the variable pulse-amplitude-modulated voltage input to the sensor 10 by the pulse power supply module 20 is in a fixed pattern, such as the pattern shown in FIG. 6. The pulse of the pulse-amplitude-modulated voltage can be maintained for a specific period, such as 3–5 seconds, to ensure the membrane temperature of the sensing element reaches a steady temperature. However, a short period, such as 1 second or hundreds of milliseconds, is also acceptable.

Further, the variable pulse-amplitude-modulated voltage input to the sensor 10 should be set such that the highest voltage pulse enables the membrane temperature to exceed the preferred temperature of the sensing element. For example, the preferred temperature for carbon monoxide is below 300° C., and the preferred temperature for hydrogen exceeds 300° C. Consequently, if an embodiment of the present invention is applied in gas identification of carbon monoxide and hydrogen, it is necessary to modulate the pulse power supply module 20 so that the highest voltage pulse of the variable PAM signal enables the membrane temperature of the sensor 10 to exceed 300° C.

The present invention can be applied to identify various gases or volatile chemical matters. For example, the present invention can be used in poisonous gas identification in a chemical laboratory, or applied as an "electric nose" technique for wine identification or perfume manufacturing process. Other possible applications of the present invention include odor identification in lavatory environments or hazardous gas identification in industry.

While the present invention has been described with reference to the preferred embodiments thereof, it is to be understood that the invention is not limited to the described embodiments or constructions. On the contrary, the invention is intended to cover various modifications and similar arrangements as would be apparent to those skilled in the art. Therefore, the scope of the appended claims should be accorded the broadest interpretation so as to encompass all such modifications and similar arrangements.

What is claimed is:

1. An intelligent gas identification system, comprising:
   a sensor disposed in a specific environment, the sensor having a voltage input element, an output element and a sensing element;
   a pulse power supply module connected to the voltage input element and sending a variable pulse-amplitude-modulated voltage to the sensor through the voltage input element, so that the sensor outputs an outgoing signal through the output element; and
   a processing device storing a plurality of chemical matter characteristics signals and receiving the outgoing signal from the output element of the sensor;
   wherein the processing device receives the outgoing signal and compares the outgoing signal with the chemical matter characteristics signals to determine an identification result for the gas in the specific environment.

2. The intelligent gas identification system according to claim 1, wherein the outgoing signal comprises a pulse amplitude voltage signal.

3. The intelligent gas identification system according to claim 1, wherein the sensing element comprises a membrane of a metallic oxide.

4. The intelligent gas identification system according to claim 3, wherein the metallic oxide comprises tin oxide ($SnO_2$).

5. The intelligent gas identification system according to claim 1, wherein the identification result for the gas comprises composition of the gas.

6. The intelligent gas identification system according to claim 5, wherein the identification result for the gas comprises concentration of the respective constituents of the gas.

7. A method of gas identification, comprising the steps of:
   providing a sensor in a specific environment;
   sending a variable pulse-amplitude-modulated voltage to the sensor, so that the sensor outputs an outgoing signal corresponding to gas in the specific environment; and
   comparing the outgoing signal with a plurality of chemical matter characteristics signals to determine an identification result for the gas in the specific environment.

8. The method of gas identification according to claim 7, wherein the chemical matter characteristics signals are obtained by:
   disposing the sensor to a plurality of predetermined chemical matters and sending a variable pulse-amplitude-modulated voltage to the sensor respectively, so that the sensor outputs each of the chemical matter characteristics signals corresponding to each of the predetermined chemical matters; and
   storing the chemical matter characteristics signals in a database.

9. The method of gas identification according to claim 7, wherein the outgoing signal comprises a pulse amplitude voltage signal.

10. The method of gas identification according to claim 7, wherein the sensing element comprises a membrane of a metallic oxide.

11. The method of gas identification according to claim 10, wherein the metallic oxide comprises tin oxide ($SnO_2$).

12. The method of gas identification according to claim 7, wherein the identification result for the gas comprises composition of the gas.

13. The method of gas identification according to claim 12, wherein the identification result for the gas comprises concentration of the respective constituents of the gas.

* * * * *